(12) United States Patent
Novack et al.

(10) Patent No.: US 9,066,862 B2
(45) Date of Patent: *Jun. 30, 2015

(54) SELF EMULSIFIED COMPOSITIONS

(75) Inventors: Candice DeLeo Novack, Suffern, NY (US); Amitabh Bansal, Hoboken, NJ (US)

(73) Assignee: Avon Products, Inc, New York, NY (US)

( * ) Notice: Subject to any disclaimer, the term of this patent is extended or adjusted under 35 U.S.C. 154(b) by 117 days.

This patent is subject to a terminal disclaimer.

(21) Appl. No.: 13/294,665

(22) Filed: Nov. 11, 2011

(65) Prior Publication Data

US 2013/0121934 A1 May 16, 2013

(51) Int. Cl.
| | |
|---|---|
| *A61K 8/88* | (2006.01) |
| *A61K 8/06* | (2006.01) |
| *A61Q 1/02* | (2006.01) |
| *A61Q 1/06* | (2006.01) |
| *A61Q 1/10* | (2006.01) |
| *A61Q 17/02* | (2006.01) |
| *A61Q 17/04* | (2006.01) |
| *A61Q 19/02* | (2006.01) |
| *A61Q 19/00* | (2006.01) |
| *A61K 8/81* | (2006.01) |
| *A61K 8/891* | (2006.01) |
| *A61K 8/898* | (2006.01) |

(52) U.S. Cl.
CPC ... *A61K 8/06* (2013.01); *A61Q 1/02* (2013.01); *A61Q 1/06* (2013.01); *A61Q 1/10* (2013.01); *A61Q 17/02* (2013.01); *A61Q 17/04* (2013.01); *A61Q 19/02* (2013.01); *A61Q 19/00* (2013.01); *A61K 8/8164* (2013.01); *A61K 8/891* (2013.01); *A61K 8/898* (2013.01); *A61K 2800/884* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 4,956,129 A | 9/1990 | Scher et al. | |
| 6,238,657 B1* | 5/2001 | Lin et al. | 424/70.12 |
| 6,361,765 B1 | 3/2002 | Emslie et al. | |
| 2002/0040065 A1* | 4/2002 | Scher et al. | 516/98 |
| 2004/0234475 A1* | 11/2004 | Lannibois-Drean et al. | 424/70.12 |
| 2009/0035246 A1 | 2/2009 | Do | |
| 2010/0093930 A1 | 4/2010 | Guo et al. | |

FOREIGN PATENT DOCUMENTS

| | | | | |
|---|---|---|---|---|
| WO | 2009139884 A1 | 11/2009 | | |
| WO | 2010068891 A2 | 6/2010 | | |
| WO | WO 2010/068891 | * 6/2010 | | A61K 8/72 |
| WO | 2010/122246 A2 | 10/2010 | | |

OTHER PUBLICATIONS

U.S. Appl. No. 13/294,562, filed Nov. 11, 2011, C. Novack et al.

* cited by examiner

*Primary Examiner* — Brian Gulledge
(74) *Attorney, Agent, or Firm* — David M. Joyal; Joan M. McGillycuddy

(57) ABSTRACT

Provided are cosmetic compositions of incompatible cosmetic composition provided long term stability by the interfacial reaction of two immiscible polymers having complementary reactive pair functional groups.

22 Claims, 2 Drawing Sheets a. reaction product of two monofunctional molecules mobile interface b. reaction product of one monofunctional and one multifunctional molecules partially mobile interface c. reaction product of two multifunctional molecules immobile interface

SELF EMULSIFIED COMPOSITIONS

FIELD OF INVENTION

The present invention relates to in-situ compatibilizers/emulsifiers for incompatible cosmetic formulations, i.e. emulsions, colloids, etc., which comprise immiscible polymers having complementary reactive groups that interact at the interface of the incompatible cosmetic compositions to stabilize the cosmetic compositions.

BACKGROUND OF THE INVENTION

Many cosmetics and personal care products, such as concealers, creams, lotions, and mascaras, are emulsions. Emulsions are a mixture of two or more immiscible liquids, such as water/oil or oil/silicone. These emulsions provide a means of dispersing a cosmetic agent, which may be lypophilic, within water or silicone which have a more appealing feel than oils. Although beneficial for administration, emulsions are typically difficult to formulate because of the demands on cosmetic products. In order to be commercially viable the emulsion must exhibit sufficient stability to survive shipping and storage environments. For example, cosmetics are often shipped under conditions where they are exposed to temperatures that are higher and lower than standard room temperature (72° F.). Products must be stable at these temperature extremes so that they can be delivered to the customer in a form that is suitable for commercial sale. In addition, commercially acceptable cosmetics must also be shelf stable, such that they do not exhibit an inordinate degree of separation when stored for long periods of time, typically one, two to three years, and even longer in some instances. The tendency of the immiscible liquids to separate out of the emulsion and coalesce frustrates these goals.

Stabilizers/emulsifiers and/or particles may be used to stabilize the emulsion. Stabilizers/emulsions tend to be amphiphilic, i.e., possessing both polar (hydrophilic) and non-polar (lypophilic) domains. The amphiphilic ingredient facilitates compatibility between two phases that may not otherwise be compatible to form a composition that is internally stable. Typically, the dispersed phase is stabilized within the continuous phase when the emulsifier/surfactant coats the interface between the dispersed and continuous phases to reduce the surface tension.

However, several problems exist with emulsifiers. Since the emulsion is stabilized by the interfacial adsorption of the surfactants (emulsifiers), the emulsion destabilizes if the emulsifiers de-adsorb from the interface or get lost in micelles before arriving at the interface. To address these complications, emulsifiers and/or particles are often added in excess to ensure they arrive at the interface. However this is less than an ideal solution given that the cost of compatibilizing agents is often high; they can be difficult to formulate; compositions containing them are sometimes prone to premature separation, and when used in high concentrations they can be somewhat irritating for consumers having sensitive skin.

WO2009139884A1 to Hein et al. outlines reacting natural butters (and other naturally occurring triglycerides) with glycerol, in the presence of a basic catalyst, during mixing to promote compatibility between lipid and water phases. The patent application does not claim any reactive polymeric materials.

WO 2010068891 to Bui et al. discloses a self-emulsifying mascara composition, in which the self-emulsification results in rheological properties which improve the lengthening properties of the cosmetic formula. The self-emulsification occurs within an aqueous formulation and involves functional polymers.

Accordingly, there is still a need for a method of stabilizing incompatible cosmetic compositions for extended periods without the drawbacks associated with conventional emulsifiers.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that a stable emulsion composition can be obtained by providing a compatibilizer at the interface of the emulsion phases.

In one aspect of the invention, emulsion compositions are provided with enhanced stability, the compositions comprising a first phase, a second phase, and a compatibilizer that is the reaction product of a first functional polymer dispersible in the first phase and a second functional polymer dispersible in the second phase, the compatibilizer having at least one complementary reactive group pairing obtained by reacting the functional group of the first polymer and the functional group of the second polymer. Preferably, the complementary reactive group pairing is selected from the group consisting of carboxylic acid/amine, carboxylic acid/oxazoline, carboxylic acid/epoxy, amine/epoxy, amine/cyclic anhydride, amine/isocyanate, hydroxyl/cyclic anhydride, hydroxyl/carboxylic acid, and combinations thereof.

In another aspect of the invention, the compatibilizer is formed interfacially between the continuous phase and disperse phases upon admixing of the first and second phases each containing their respective dispersible functional polymers to effect compatibilizer formation by in-situ reaction of the polymers.

The at least one polymer dispersed in the first phase and the at least one polymer dispersed in the second phase, each polymer having at least one reactive functional group component adapted to form the at least one complementary reactive group pairing. Suitable reactive functional groups for each dispersible polymer may be selected either from (i) a first group consisting of an amine, a carboxylic acid, or a hydroxyl group, or from (ii) a second group consisting of an amine, a carboxylic acid, a cyclic anhydride, an epoxy, an isocyanate, an oxazoline, or a silicone hydride group, the selected reactive first and second functional group each being adapted to form said complementary reactive group pairing. Each polymer may contain two or more different reactive groups for that polymer, and the compatibilizer thus obtained may comprise two or more of the recited group pairings.

In a further embodiment, the emulsion composition is selected from emulsions consisting of oil-in-silicone, silicone-in-oil, oil-in-oil, fluoropolymer-in-oils, oil-in-fluoropolymer, fluoropolymer-in-silicone, or silicone-in-fluoropolymer emulsion. These compositions comprise a disperse phase stably dispersed in a continuous phase.

In a further aspect of the invention, the dispersible polymers, i.e., the first phase dispersible polymer or the second phase dispersible polymers are natural or synthetic polymers. In a further embodiment, the natural polymers are selected from chitin, chitosan, polysaccharides, and combinations thereof, and in a further embodiment the synthetic polymers are selected from polyolefins, polyether, polyesters, polysiloxanes, polyamides, polyacrylates, polyurethanes, polyphosphazenes, polyvinylpyrolidones, and combinations thereof. The functional groups attached to these dispersible polymers are pendant to, endcapped on, or are within the backbone chain of the dispersible polymers.

In a preferred aspect of the invention, the complementary reactive group pairing of the current invention is amine/cyclic anhydride. In a further aspect of the invention, the interface reaction occurs at a temperature range from about 20° C. to about 100° C., and in further embodiments at a pH of 1 to 14, preferably about a pH of about 3.5 to about 9.5. In a further embodiment, the interface reaction occurs in about one minute to about one hour after the continuous phase dispersible polymer and the disperse phase dispersible polymer are blended and preferably in about one minute to about ten minutes. The interface reaction also preferably does not produce a leaving group. Further, the interface reaction may occur before formulation of the cosmetic composition upon blending of the immiscible polymers or upon sequential application of the immiscible polymers to an integument in order to form a stabilized bi-layer in-situ.

In a further aspect, the emulsion compositions are useful in the cosmetic field for topical application to human integument, e.g., skin, lips, hair, nails, etc., and may be further comprise colorants, pigments, emollients, skin-benefit agents, botanical extracts, rheology modifiers, film formers, aesthetic modifiers, other emulsifiers, or a combination thereof.

Further aspects of the invention are directed to double emulsions wherein the non-aqueous emulsion of the present invention is further emulsified with a hydrous phase to form a double emulsion selected from the group consisting of silicone-in-oil-in water, oil-in-silicone-in-water, fluoropolymer-in-silicone-in-water, silicone-in-fluoropolymer-in-water, fluoropolymer-in-oil-in-water, and oil-in-fluoropolymer-in-water.

The current invention is further directed to a method for producing emulsion compositions having long term stability comprising the steps of providing a first phase having at least one functional polymer dispersed therein, the polymer having at least one reactive functional group that is one member of a complementary reactive pair; providing a second phase having at least one functional polymer dispersed therein, the polymer having at least one reactive functional group that is a different member of the complementary reactive pair; and forming a compatibilizer at the interface of the first phase and the second phase by admixing the first phase and the second phase to initiate a reaction between the dispersed polymers at the interface.

In still a further aspect, the invention is directed to a kit comprising a composition of claim 1. In a further embodiment of the kit the continuous phase containing the continuous phase polymer and the disperse phase containing the disperse phase polymer are separate components in the kit. In a further embodiment of the method of the present invention the phases are conjoined, for example by applying the first phase as a bottom coat and the second layer as a top coat on the integument, with the reaction occurring at the interface of the layers.

These and other aspects of the present invention will be better understood by reference to the following detailed description and accompanying figures.

DESCRIPTION OF THE DRAWINGS

FIG. 1A depicts the interactions of monofunctional polymers at the interface of two immiscible liquids; FIG. 1B depicts the interactions of a monofunctional polymer and a multifunctional polymer at the interface of two immiscible liquids; and FIG. 1C depicts the interactions of multifunctional polymers at the interface of two immiscible liquids.

DETAILED DESCRIPTION

Figure 1:
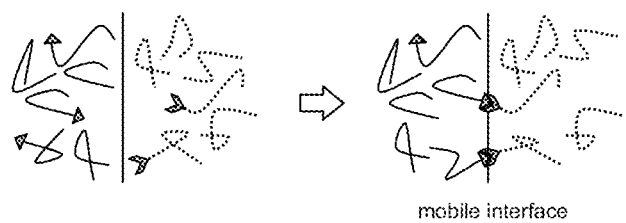
FIGS. 1A-1C depicts differences in interfacial reactions of emulsifiers/compatibilizers.
Figure 1:
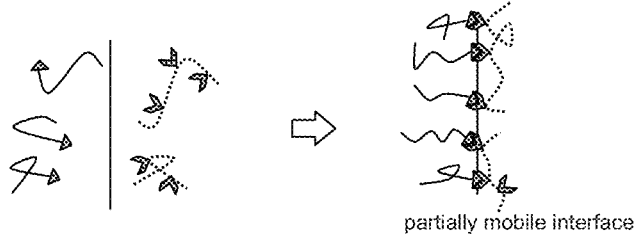
Figure 1:
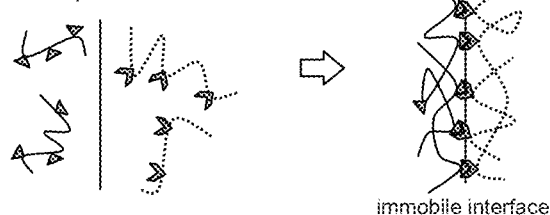

U.S. patent application Ser. No. 13/294,562, titled "Cosmetic Compositions Of Reactively Blended Copolymers," filed contemporaneously herewith on Nov. 11, 2011, is incorporated herein by reference in entirety All terms used herein are intended to have their ordinary meaning unless otherwise provided.

As used herein, the term "consisting essentially of" is intended to limit the invention to the specified materials or steps and those that do not materially affect the basic and novel characteristics of the claimed invention, as understood from a reading of this specification. The term "compatibilizer" means the reaction product of the dispersible polymers of the present invention that are capable of providing stability to incompatible phases of a composition. The term "dispersible" as it relates to the functional polymers used to form the compatibilizer means that the polymer is compatible in and can be homogeneously incorporated within the phase in which it is provided. All percentages are by weight based on the total weight of the composition, unless otherwise indicated.

This invention involves using a compatibilizer to stabilize emulsion compositions, including colloid compositions. In particular, the compatibilizer is the reaction product of a first functional polymer dispersible in the first phase and a second functional polymer dispersible in the second phase, the compatibilizer having at least one complementary reactive group pairing obtained by reacting the functional group of the first polymer and the functional group of the second polymer.

The emulsion compositions comprise a first phase (hereinafter the continuous phase), a second phase (hereinafter the disperse phase), and the compatibilizer that is present in the emulsion composition substantially at the interface of the continuous and disperse phases. Preferably, the complementary reactive group pairing is selected from the group consisting of carboxylic acid/amine, carboxylic acid/oxazoline, carboxylic acid/epoxy, amine/epoxy, amine/cyclic anhydride, amine/isocyanate, hydroxyl/cyclic anhydride, hydroxyl/carboxylic acid, and combinations thereof. As used herein the terms first phase, continuous phase, second phase, and disperse phase also refer to the compositions of those phases, whether in emulsified form in the emulsion composition or in premix form prior to use in forming the compositions of the present invention. Accordingly, the disperse and continuous phases may be discrete compositions within a kit for forming the emulsion compositions or discrete compositions useful in the manufacture of the emulsion compositions.

The at least one polymer dispersed in the continuous phase and the at least one polymer dispersed in the dispersed phase each have at least one reactive functional group component adapted to form the at least one complementary reactive group pairing. Suitable reactive functional groups for each dispersible polymer may be selected either from (i) a first group consisting of an amine, a carboxylic acid, or a hydroxyl group, or from (ii) a second group consisting of an amine, a carboxylic acid, a cyclic anhydride, an epoxy, an isocyanate, an oxazoline, or a silicone hydride group, the selected reactive first and second functional group each being adapted to form said complementary reactive group pairing.

In another aspect of the invention one of the functional polymers may comprise two or more of the same functional group. In yet another embodiment each functional polymer may comprise two or more of the same functional group. The incorporation of two (or more) functional groups in a polymer dispersed in one of the phases of the emulsion composition advantageously results in the formation of a partially mobile interface as depicted in FIG. 1B. The incorporation of two (or more) functional groups in each polymer dispersed in its respective phase of the emulsion composition advantageously results in the formation of an immobile interface as depicted in FIG. 1C.

Most preferably, the compatibilizer is formed interfacially between the continuous phase and disperse phases upon admixing of the first and second phases each containing their respective dispersible functional polymers, especially in the case of a compatibilizer intended to form a partially mobile interface or an immobile interface, as noted above.

While the compositions of the invention are especially useful in the cosmetic field, the use of the compatibilizers of the invention are readily seen to have utility in related applications, such as pharmaceutical preparations, dermatological formulations, wellness products, personal care products, and the like.

A. Emulsion Compositions

Compostions benefiting from the compatibilizers of the current invention include dispersed systems comprising two or more mutually insoluble or sparingly soluble liquids such as colloids or emulsions. One of the liquids is usually present in excess and is termed the continuous or external phase, while the liquid dispersed in it is termed the dispersed, discontinuous or internal phase. The emulsions may include aqueous emulsions such as water-in-oil (W/O), oil-in-water (O/W), water-in-silicone (W/S), silicone-in-water (S/W), wax-in-water (Wx/W), water-in-fluoropolymer (W/F), fluoropolymer-in-water (F/W), and polyol-in-oil. The emulsions may further include anhydrous emulsions including, but not limited to, oil-in-silicone (O/S), silicone-in-oil (S/O), oil-in-oil (O/O), fluoropolymer-in-oil (F/O), oil-in-fluoropolymer (O/F), fluoropolymer-in-silicone (F/S), silicone-in-fluoropolymer (S/F), oil-in-wax, wax-in-oil (Wx/O), wax-in-silicone, or silicone-in-wax. Anhydrous emulsions are preferred, and in certain embodiments of the current invention aqueous emulsions are excluded.

Compounds suitable for use as the oil phase in certain emulsions may include without limitation, vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils.

Hydrocarbon oils include those having 6-20 carbon atoms, more preferably 10-16 carbon atoms. Representative hydrocarbons include decane, dodecane, tetradecane, tridecane, and C8-20 isoparaffins. Paraffinic hydrocarbons are available from Exxon under the ISOPARS trademark, and from the Permethyl Corporation. In addition, C8-20 paraffinic hydrocarbons such as C12 isoparaffin (isododecane) manufactured by the Permethyl Corporation having the tradename Permethyl 99ATM are also contemplated to be suitable. Various commercially available C16 isoparaffins, such as isohexadecane (having the tradename Permethyl®) are also suitable. Examples of preferred volatile hydrocarbons include polydecanes such as isododecane and isodecane, including for example, Permethyl-99A (Presperse Inc.) and the C7-C8 through C12-C15 isoparaffins such as the Isopar Series available from Exxon Chemicals. A representative hydrocarbon solvent is isododecane.

Further, the silicone phase in the emulsions may comprise one or more volatile and/or non-volatile silicone oils. Volatile silicones include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethylcyclotetrasiloxane, and decamethyl-cyclopentasiloxane. Suitable dimethicones are available from Dow Corning under the name Dow Corning 200® Fluid and have viscosities ranging from 0.65 to 600,000 centistokes or higher. Suitable non-polar, volatile liquid silicone oils are disclosed in U.S. Pat. No. 4,781,917, herein incorporated by reference in its entirety. Additional volatile silicone materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C., whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G.E. Silicones), GE 7207 and 7158 (General Electric Co.); and SWS-03314 (SWS Silicones Corp.). Linear, volatile silicones include low molecular weight polydimethylsiloxane compounds such as hexamethyldisiloxane, octamethyltrisiloxane, decamethyltetrasiloxane, and dodecamethylpentasiloxane, to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone. The volatile and non-volatile silicone oils may optionally be substituted with various functional groups such as alkyl, aryl, amine groups, vinyl, hydroxyl, haloalkyl groups, alkylaryl groups, and acrylate groups, to name a few.

Waxes, comprising one of the phases of an emulsion include, but are not limited to, rice bran wax, carnauba wax, ouricurry wax, candelilla wax, montan waxes, sugar cane waxes, ozokerite, polyethylene waxes, Fischer-Tropsch waxes, beeswax, microcrystalline wax, silicone waxes, fluorinated waxes, and any combination thereof.

Also, fluoropolymers suitable for use within the emulsions may include, but are not limited to, polytetrafluoroethylene (PTFE, Teflon), perfluoroalkoxy polymer resin (PFA, Teflon), fluorinated ethylene-propylene (FEP, Teflon), ethylene tetrafluoroethylene (ETFE), Ethylene chlorotrifluoroethlyene (ECTFE), hexafluoroisopropyl methacrylate and 1H, 1H perfluorobutyl methacrylate.

B. Polymers

The functional dispersible polymers of the current invention may be selected from natural or synthetic oligomers or polymers, or derivatives thereof having suitable compatibility, e.g., dispersibility, with the phase of the composition, i.e., continuous or dispersed phase, to which the polymer will be incorporated.

Suitable naturally occurring polymers may include, but are not limited to polysaccharides and natural gums including nut not limited to pullan, carrageen, glycon, celluloses, such as hydroxy cellulose, amylose, chitosan, N,O-carboxymethylchitosan, algin and alginic acid, agar, pectin, starch, dextran, dextrin, cyclodextrin, konjac glucomannan, chitin, pustulan, heparin, cardlan, hyaluronic acid, xantham, combinations and derivatives thereof.

Suitable synthetic polymers may include, but are not limited to, polyolefins; polyether such as polyethylene glycol, polypropylene glycol, polytetramethylene glycol, polytetramethylene ether glycols, polyethylene oxide, or polypropylene oxide; polyester; polysiloxane such as polydimethylsiloxane, amidomethicones, or phenyltrimethicones; polyamide; polyacrylate such as sodium polyacrylate, carbomers, or carbapols; polyurethane; polyphosphazene; polyvinylpyrolidone; mixtures or combinations thereof.

These functional dispersible polymers may include linear or branched versions of the above noted polymers.

The functional dispersiblepolymers, those compatible with the continuous phase and those compatible with the dispersed phase, each contain a member of a complementary reactive pair of functional groups. This permits the functional dispersible polymers to react, network, or crosslink at the interface upon admixing. The complementary reactive pairs are disclosed within Table 1 below.

TABLE 1

Complementary pairs of reactive functional groups

| Pair | First Functional Group of Pair | Second Functional Group of Pair |
|---|---|---|
| 1 | carboxylic acid | amine* |
| 2 | amine | epoxy |
| 3 | carboxylic acid | oxazoline |
| 4 | carboxylic acid | epoxy |
| 5 | amine | cyclic andhydride |
| 6 | amine | Isocyanate |
| 7 | hydroxyl | cyclic andhydride |
| 8 | hydroxyl | carboxylic acid |
| 9 | amine | carboxylic acid |

*where the amine group is aliphatic, aromatic, amino acid, peptide or an amine-silicone The above-noted reactive pairs are preferably used when compatibilizing anhydrous systems. When compatibilizing aqueous systems, the preferred complementary reactive pairs d are carboxylic acid/amine, carboxylic acid/oxazoline, amine/epoxy, amine/cyclic anhydride, or amine/isocyanate. In either instance, the preferred complementary reaction pair is maleic anhydride/amine.

The members of the complementary reactive pairs may be pendant to, endcapped on, or incorporated within the backbone of the polymer. The pendant and endcapped functional groups are preferred with the pendant groups being most preferred.

Each of the functional polymers have at least one functional group, usually at least two reactive groups, and may have greater than two functional groups. As demonstrated in FIGS. 1A-C, as the number of functional groups on the dispersible polymers increase, the mobility of the interfacial compatibilizer decreases. Thus, the greater the number of functional groups, the greater the amount of networking or cross-linking that occurs between the polymers rendering the interface increasingly immobile and the emulsion composition more stabilized as shown in FIG. 1C.

In one embodiment the first functional polymer and/or the second functional polymer has two or more functional groups thereon, each of the functional groups being identical in respect of each polymer (e.g., the first polymer may have two or more amine groups and the second polymer may have two or more epoxy groups, i.e, Pair 2 in Table 1).

In another embodiment one of said first or second polymers has two or more different functional groups thereon, each of said different functional groups being adapted to form different complementary reactive group pairings with the functional group on the other of the polymers (e.g., the first polymer may have amine and hydroxyl groups and the second polymer may have a cyclic anhydride to form Pairs 5 and 7 of Table 1).

In another embodiment both of said first and second polymers have two or more different functional groups thereon, each of said different functional groups on the first polymer forming two or more different complementary reactive group pairings with the functional groups on the other of the polymers (e.g., amine and hydroxyl on the first polymer and cyclic anhydride and carboxylic acid on the second polymer, i.e., with Pairs 5, 7, 8 and 9 being available for formation).

Examples of commercially available polymers suitable for the reactions of the current invention.

TABLE 2

Commercially available materials which have functional groups necessary for interfacial coupling

| Functional Group | Trade Name of Functional Polymer (Vendor) | INCI Name of Functional Polymer |
|---|---|---|
| carboxylic acid | Diacid 1550 (Westvaco Corporation) | Cyclocarboxypropyloleic Acid |
| amine | AMS-162 (Gelest, Inc.) | amino propyl polydimethylsiloxane |
|  | KF8004 (Shin Etsu Inc.,) | amodimethicone |
| hydroxyl | Carbowax PEG 400 (The Dow Chemical Company) | PEG 8 |
| Epoxy | Polamine E-125 (Toho Chemical Industry Co., Ltd.) | Adipic Acid/Epoxypropyl Diethylenetriamine Copolymer |
| Oxazoline | Cycloceramide (Laboratoires Expanscience) | Undecyl Dimethyl Oxazoline |
| Isocyanate | Polymethylene Polyphenylisocyanate Polymer with Hexamethylene Diamine (International Flavors & Fragrances, Inc.) | Hexamethylenediamine/MDI Copolymer |
| cyclic anhydride | Marlene CP-80 (Lion Copolymer) | Ethylene/Maleic anhydride/Propylene Copolymer |
|  | SMA (Sartomer) | Styrene-maleic anhydride |
|  | Gantrez AN (ISP) | Poly(methylvinylether-co-maleic anhydride) |
|  | Lotader (Arkema) | Ethylene-acrylic-ester-maleic anhydride |

The at least two immiscible polymers comprising complementary functional reactive groups are present in a concentration ranging from about 0.05% to 50% by weight, preferably from about 0.1% to 20% by weight, and more preferably from about 0.25% to 10% by weight, relative to the total weight of the composition as disclosed herein.

C. Interfacial Reaction

The dispersible polymers may then be admixed to initiate the interfacial reaction that generates the in-situ compatibilizer. In some instances this reaction may occur prior to the addition of the polymers to an incompatible composition, but will most usually occur coextensively with the development of the composition, and may also occur sequentially during application to the integument—i.e., one phase laid down on the integument followed by the second phase in order to form a networked or cross-linked bilayer in situ.

These reactions may occur at temperatures ranging from 20° C. to 120° C., preferably about 20° C. to about 75° C., and most preferably about 20° C. to about 50° C. Similarly, the reaction will proceed at pHs of about 1 to 14, more preferably about 3.5 to 9.5 and most preferably about 5 to 8. Ideally, the reaction will proceed under ambient conditions without the need for catalysts or activators. Although the reaction of the complementary reactive groups may result in a leaving group as a result of the leaving group, it is preferred that the complementary reactive groups be selected or the reaction parameters be optimized such that the reaction does not generate a leaving group.

The interfacial reaction of the current invention generally finishes within about one minute to about one hour of contact of the two immiscible reactive polymers, preferably within about one minute to thirty minutes, most preferably within one to ten minutes.

The compatibilized compositions of the current may be further combined with a hydrous phase to form a double emulsion selected from the group consisting of silicone-in-oil-in-water, oil-in-silicone-in-water, fluoropolymer-in-silicone-in-water, silicone-in-fluoropolymer-in-water, fluoropolymer-in-oil-in-water, polyol-in-oil-water, and oil-in-fluoropolymer-in-water, wherein the hydrous phase is emulsified using a compatibilizer of the invention or a conventional emulsifier as is known in the art.

D. Useful Cosmetic Actives and Excipients

The emulsions of the invention are especially useful in the preparation of cosmetic compositions, and may optionally comprise cosmetic excipients as known to those practicing the cosmetic arts, including but not limited to, fillers, emulsifying agents, surfactant active agents, film formers, plasticizers, solvents, chelating agents, gelling agents, thickeners, anti-foaming agents, binders, bulking agents, pH adjusters, preservatives, stabilizers, photostabilizing agents, viscosity and/or rheology modifiers, and combinations thereof.

The emulsion compositions of the invention may optionally comprise cosmetic actives as known to those practicing the cosmetic arts, including but not limited to, antioxidants, emollients, humectants, moisturizers, vitamins, sunscreens, keratolyses, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, anti-acne agents, anesthetics, antiseptics, insect repellents, skin cooling compounds, skin protectants, skin penetration enhancers, exfollients, lubricants, fragrances, colorants, depigmenting agents, hypopigmenting agents, and mixtures thereof.

In addition to the foregoing, the cosmetic emulsion compositions of the invention may contain any other compound for the treatment of skin disorders. The actives and/or excipients may work in concert with the composition to achieve cumulative or synergistic improvements in the aesthetic appearance of the integument to which it is applied. The actives and excipients will typically be homogeneously distributed in one of the phases of the compatibilized emulsion.

The cosmetic compositions of the current invention may include additional emulsifiers such as emulsifying waxes, emulsifying polyhydric alcohols, polyether polyols, polyethers, mono- or di-ester of polyols, ethylene glycol monostearates, glycerin mono-stearates, glycerin di-stearates, silicone-containing emulsifiers, soya sterols, fatty alcohols such as cetyl alcohol, fatty acids such as stearic acid, fatty acid salts, and mixtures thereof. The preferred emulsifiers include soya sterol, cetyl alcohol, stearic acid, emulsifying wax, and mixtures thereof. Other specific emulsifiers that can be used in the composition of the present invention include, but are not limited to, one or more of the following: sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, Steareth-10, and Steareth-20, to name a few. Additional emulsifiers are provided in the INCI Ingredient Dictionary and Handbook 11th Edition 2006, the disclosure of which is hereby incorporated by reference.

These emulsifiers typically will be present in the composition in an amount from about 0.001% to about 10% by weight, in particular in an amount from about 0.01% to about 5% by weight, and more preferably, below 1% by weight.

In some, but not all, embodiments, the compositions may include additional film-forming polymers. Particular mention may be made of polymers that provide good transfer-resistance, including silicone acrylate copolymers, such as those having the INCI names Butyl Acrylate/Hydroxypropyl Dimethicone Acrylate Copolymer (CTFA Monograph ID 12998), Acrylates/Dimethicone Copolymer (CTFA Monograph ID 10082), and Acrylates/Ethylhexyl Acrylate/Dimethicone Methacrylate Copolymer (CTFA Monograph ID 16592). Other suitable film formers include, without limitation, polyolefins, polyamides, polyesters, polyimides, polyurethanes, acrylates, and the like.

In some embodiments, the compositions may include from about 0.1% to about 50%, typically from about 1% to about 20%, by weight of a wax component. The waxes may be low melt waxes such as higher chain alkanes, including for example, n-octadecane (MP~28-30° C.), n-nonadecane (MP~32° C.), and n-eicosane (MP~37° C.), or high melt waxes including, without limitation, many traditional waxes that are derived, for example, from animals, insects, vegetables, minerals, or petroleum, as well as synthetic waxes, Fisher Tropsch waxes, and mixtures of any of the foregoing waxes. Specific mention is made of carnauba, paraffin wax, candelilla, castor, beeswax, microcrystalline wax, ceresin, ozokerite, polyethylene wax, low MW polyalkyacrylate, and silicone waxes, such as alkyl silicones, or any combinations thereof.

Colorants may include, for example, organic and inorganic pigments and pearlescent agents. Suitable inorganic pigments include, but are not limited to, titanium oxide, zirconium oxide and cerium oxide, as well as zinc oxide, iron oxide, chromium oxide and ferric blue. Suitable organic pigments include barium, strontium, calcium, and aluminium lakes and carbon black. Suitable pearlescent agents include mica coated with titanium oxide, with iron oxide, or with natural pigment.

Various fillers and additional components may be added. Fillers are normally present in an amount of about 0 weight % to about 20 weight %, based on the total weight of the composition, preferably about 0.1 weight % to about 10 weight %. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

In one embodiment of the invention, the compositions may include additional skin actives such as, but not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, salicylic acid or salicylates, thiodipropionic acid or esters thereof, and advanced glycation end-product (AGE) inhibitors to achieve cumulative or synergistic improvements in the aesthetic appearance of the treated skin.

In a specific embodiment, the composition may comprise at least one additional botanical, such as, for example, a botanical extract, an essential oil, or the plant itself. Suitable botanicals include, without limitation, extracts from *Abies pindrow, Acacia catechu, Alisma orientate, Aloe, Amorphophallus campanulatus, Anogeissus latifolia, Asmunda japonica, Azadirachta indica, Butea frondosa, Butea monosperma, Cedrus deodara*, Chamomile, *Derris scandens, Portulaca oleracea, Eclipta prostrala, Emblica officinalis, Erythina indica, Ficus benghalensis, Glycyrrhiza glabra, Humilus scandens, Ilex purpurea Hassk, Innula racemosa, Ixora chinensis, Ligusticum chiangxiong, Ligusticum lucidum, Mallotus philippinensis, Medemia noblis, Melicope hayesii, Mimusops elengi, Morinda citrifolia, Moringa oleifera, Naringi crenulata, Nerium indicum, Piper betel, Portulaca oleracea, Pouzolzia petandra, Psoralea corylifolia, Rhinacanthus nasutus, Sapindus rarek, Sesbania grancliflora, Stenoloma chusana, Terminalia bellerica, Tiliacora triandra*, tomato glycolipid and mixtures thereof.

The composition may comprise additional active ingredients having anti-aging benefits, as it is contemplated that synergistic improvements may be obtained with such combinations. Exemplary anti-aging components include, without limitation, botanicals (e.g., *Butea frondosa* extract); phytol, thiodipropionic acid (TDPA) and esters thereof; retinoids (e.g., all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In another embodiment, the topical compositions of the present invention may also include one or more of the following: a skin penetration enhancer, an emollient, a skin plumper, an optical diffuser, a sunscreen, an exfoliating agent, and an antioxidant.

An emollient provides the functional benefits of enhancing skin smoothness and reducing the appearance of fine lines and coarse wrinkles. Examples include isopropyl myristate, petrolatum, isopropyl lanolate, silicones (e.g., methicone, dimethicone), oils, mineral oils, fatty acid esters, or any mixtures thereof. The emollient may be preferably present from about 0.1 wt % to about 50 wt % of the total weight of the composition.

A skin plumper serves as a collagen enhancer to the skin. An example of a suitable, and preferred, skin plumper is palmitoyl oligopeptide. Other skin plumpers are collagen and/or other glycosaminoglycan (GAG) enhancing agents. When present, the skin plumper may comprise from about 0.1 wt % to about 20 wt % of the total weight of the composition.

An optical diffuser is a particle that changes the surface optometrics of skin, resulting in a visual blurring and softening of, for example, lines and wrinkles. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. When present, the optical diffuser may be present from about 0.01 wt % to about 20 wt % of the total weight of the composition.

Additionally, sunscreens may also be added to the cosmetic composition of the current invention. The cosmetic composition of the current invention may increase the effectiveness of the sunscreen by fixing it in place over the keratinaceous integument to which it is applied. Alternatively, the sunscreen may be added to the cosmetic composition when it is used to enhance the color retention of artificial hair coloring to additive or synergistic effect as the sunscreen may counteract environmental stresses on the coloring. Non-limiting examples of sunscreens include benzophenones, bornelone, butyl paba, cinnamidopropyl trimethyl ammonium chloride, disodium distryrylbiphenyl disulfonate, paba, potassium methoxycinnamate, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, diethanolamine methoxycinnamate, glyceryl aminobenzoate, octylmethoxycinnamate, titanium dioxide, zinc oxide, cinoxate, oxybenzone, Padimate O, red petrolatum, and mixtures thereof. When present, the sunscreen may comprise from about 0.01 wt % to about 70 wt % of the composition.

Suitable exfoliating agents include, for example, alpha-hydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A preferred exfoliating agent is glycolic acid. When present, the exfoliating agent may comprise from about 0.1 wt % to about 80 wt % of the composition.

An antioxidant functions, among other things, to scavenge free radicals from skin to protect the skin from environmental aggressors. Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant preferably from about 0.001 wt % to about 10 wt %, and more preferably from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents such as bentonite, smectite, magnesium aluminum silicate and lithium magnesium silicate; metal chelating agents such as EDTA; pigments such as zinc oxide and titanium dioxide; colorants; emollients; and humectants.

The composition may be formulated in a variety of product forms, such as, for example, a lotion, cream, serum, spray, aerosol, cake, ointment, essence, gel, paste, patch, pencil, towelette, mask, stick, foam, elixir, concentrate, and the like, particularly for topical administration. Preferably the composition is formulated as a lotion, cream, ointment, or gel.

The present invention provides a method for enhancing the long term stability of otherwise incompatible cosmetic formulations such as emulsions using the compositions of the current invention. Namely, the method involves, admixing with the continuous phase of the emulsion at least one immiscible polymer compatible therewith having at least one reactive functional group, admixing with the disperse phase at least one immiscible polymer compatible therewith having at least one reactive functional group, wherein the reactive groups on the continuous phase compatible polymer and the disperse phase polymer form a complementary reactive air such that when the formulation is blended the two polymers react at the interface generating an in-situ compatibilizer. In alternative embodiments of the inventive method, the polymers may be blended prior to being incorporated into the incompatible cosmetic formulation of the polymers and their respective phases may be applied sequentially to a human integument, such as hair, skin, nails, eyelids, etc., so that a stabilized bi-layer is formed in-situ.

The present invention also provides kits or prepackaged materials containing the compositions of the present invention. These kits or prepackaged materials can provide a pre-mixed cosmetic formulation incorporating the composition of the current invention, the immiscible polymers provided separately, but in the same package as the cosmetic, hair care, or skin care composition, which then can be premixed and applied to the integument; or provided as separate immiscible polymers with their compatible phase to be applied sequentially to the integument to develop a cross-linked bilayer in situ over the integument. These kits may further include documentation related to the cosmetic composition of the current invention including, but not limited to, instructions for use, ingredient lists, and or warnings.

The following examples are meant to demonstrate certain aspects of the invention in a non-limiting fashion.

EXAMPLES

Example 1

Improved Emulsion Stability Via Reactive Emulsification

The effectiveness of the in-situ reactive emulsifier of the current invention was compared to commercially available emulsifiers in an incompatible cosmetic system of polyisobutene and dimethicone. Six emulsions were made using the formulations within Table 3 below. In particular, two positive controls, samples 2 and 3, were generated by adding Silwax CR 5016 and Silwax D02 (Siltech), alkylated silicones known to compatibilize silicone and oil compositions, to the silicone within samples 2 and 3, respectively, and blending at 80° C. for 10 minutes. Samples 4-5 are emulsions incorporating reactive polymers of the current invention, i.e. Marlene (Lion Copolymer, LLC) an ethylene-propylene copolymer with 2% wt pendant maleic anhydride groups and AMS-132 (Gelest, Inc.) a linear polydimethylsiloxane with pendant amine groups, at a ratio 2:1 to 1:2, respectively. The maleic anhydride and amine groups are able to react with each other forming an in situ emulsifier. In each sample, the appropriate amount of AMS-132 was pre-added to the silicone phase and blended at 80° C. for 10 min, and the Marlene CP80-2 was pre-added to the polyisobutene phase and blended at 80° C. for 10 min. In each of the samples, the hot silicone phase was slowly added to the hot polyisobutene phase and vigorously blended for 20 minutes. All finished emulsions were placed in 40° F. (4.44° C.) and 110° F. (43.33° C.) stability for 4 weeks.

TABLE 3

Emulsion Formulations

| Sample | Polyisobutene | Dimethicone | Silwax CR5016 | Silwax D02 | Marlene CP80-2 | AMS-132 |
|---|---|---|---|---|---|---|
| 1 Negative Control-no compatibilizer | 80 | 20 | | | | |
| 2 Positive Control 1- Silwax CR 5016 | 76 | 19 | 5 | | | |
| 3 Positive Control 2- Silwax D02 | 76 | 19 | | 5 | | |
| 4 1:2 reactive group match | 76 | 19 | | | 2.5 | 2.5 |
| 5 1:1 reactive group match | 76 | 19 | | | 3.35 | 1.65 |
| 6 2:1 reactive match | 76 | 19 | | | 4 | 1 |

Figure 2:
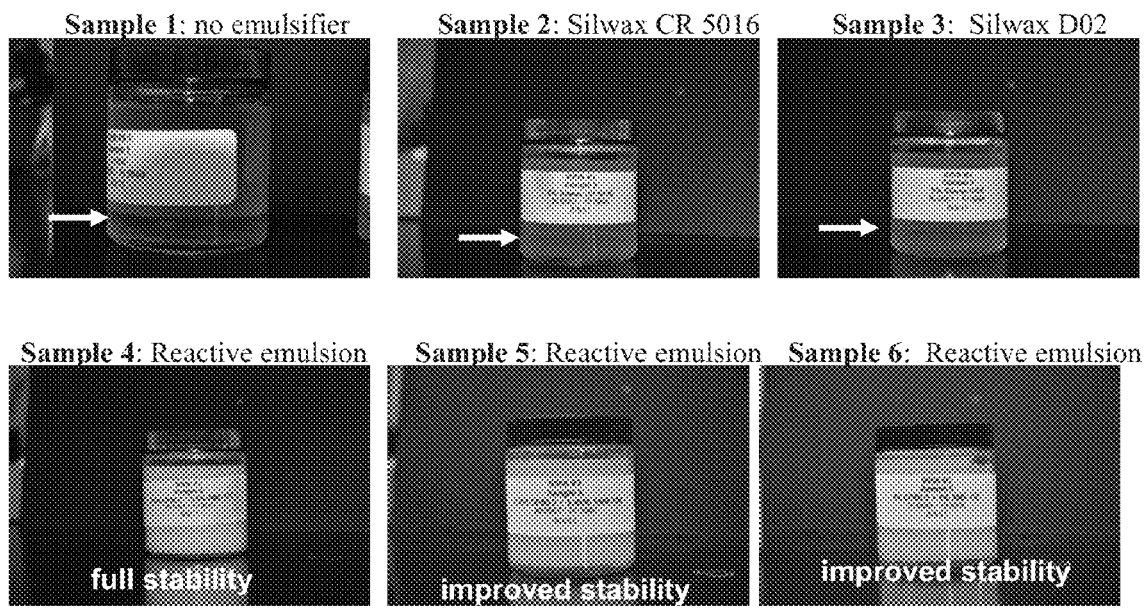
FIG. 2 compares the stability of prior art (Solutions 1-3) emulsions and self-emulsified compositions (Solutions 4-6) of the current invention, and demonstrates that the self-emulsified compositions exhibit greater stability.

FIG. 2 shows the results of the stability study. As can be seen in FIG. 2, Samples 1, 2, and 3 showed signs of large scale phase separation after one week with each formation forming two distinct layers. Surprisingly, after 4 weeks on the stability Testing, Samples 5 and 6 showed only a slight clarified layer formed at the bottom of the jar, and Sample 4 remained completely unseparated.

Example 2

Improving Lipstick Hardness

Two batches of silicone/oil emulsion lipsticks were made in accordance with Table 4 below to compare the effect of reactive emulsification on lipstick breakage. An improvement in breakage, measured by the peak force placed on the fully extended lipstick before breaking, is observed in both batches.

TABLE 4

Lipstick Formulations and Hardness Results

| Ingredient | INCI Name | Lipstick Emulsion 1 with reaction | Lipstick Emulsion 1 NO reaction | Lipstick Emulsion 2 with reaction | Lipstick Emulsion 2 NO reaction |
|---|---|---|---|---|---|
| Marlene CP80-2 | Ethylene/Maleic anhydride/propylene copolymer* | 5 | 5 | 5 | 5 |
| Ozokerite | Ozokerite | 4 | 4 | 4 | 4 |
| Polyethylene | Polyethylene | 7 | 7 | 7 | 7 |
| Dub Vinyl | Dipentaerythrityl Pentaisononanoate | 21 | 21 | 21 | 21 |
| Colorants | Colorants | 12 | 12 | 12 | 12 |
| Octyldodecanol | Octyldodecanol | 5 | 5 | 5 | 5 |
| Stearyl Dimethicone | Stearyl Dimethicone | 11 | 11 | 11 | 11 |
| Ethylhexyl Methoxycinamate | Ethylhexyl Methoxycinnamate | 7 | 7 | 7 | 7 |
| Jojoba Oil | *Simmondsia Chinensis* (Jojoba) Seed Oil | 9 | 9 | 9 | 9 |
| Polyboost | C30-45 Olefin* | 5 | 5 | 5 | 5 |
| Barshine 147 | Polyglyceryl-10 Decaoleate | 4 | 4 | 4 | 4 |
| AMS-132 | Amino Propyl Dimethicone* | 1 | 0 | 1 | 0 |
| Dimethicone | Dimethicone | 9 | 10 | 0 | 0 |
| Silshine 150 | Phenylpropyldimethylsiloxysilicate | 0 | 0 | 9 | 10 |
| | TOTAL | 100.00 | 100.00 | 100.00 | 100.09 |
| | Breakage (kg) | 0.3452 | 0.2805 | 0.3053 | 0.2779 |

*pending INCI names

Example 3

Exemplary Formulations

A. Mascara Formulations

The following example serves to provide a general formula of representative reaction emulsion based mascara composition in accordance with the present invention. Suggested ingredient ranges are provided.

TABLE 5

Mascara Formulation

| Component | Weight Range |
|---|---|
| Silicone Phase | |
| Thickeners | 1.0-2.0 |
| Film Formers | 0.5-2 |

TABLE 5-continued

Mascara Formulation

| Component | Weight Range |
|---|---|
| Preservative | 0.1-0.6 |
| Reactive silicone emulsifier (eg. Amino propyl dimethicone) | 1.0-2.0 |
| Pigments | 4.0-10.0 |
| Silicone Oil | qs 100% |
| Oil Phase | |
| Waxes | 10.0-20.0 |
| Reactive oil emulsifier (eg. Ethylene/maleic anhydride/propylene copolymer) | 1.0-2.0 |
| Emollients (eg. Oils & Esters) | 0.5-5 |
| Fillers | 0.1-1 |

B. Sunscreen

The following example serves to provide a general formula of representative reaction emulsion based sunscreen composition in accordance with the present invention. Suggested ingredient ranges are provided.

TABLE 6

Sunscreen Formulation

| Component | Weight Range |
|---|---|
| Oil Phase | |
| Sunscreen (eg. Octylmethoxycinnamate, octyl salicylate, zinc oxide, etc.) | 25-35 |
| Reactive oil emulsifier (eg. Ethylene/maleic anhydride/propylene copolymer) | 1.0-3.0 |
| Emollients (eg. Esters and Oils) | 12.0-25.0 |
| Preservative (eg. Methyl paraben) | 1.0-2.0 |

TABLE 6-continued

Sunscreen Formulation

| Component | Weight Range |
|---|---|
| Silicone Phase | |
| Silicone Oil (eg. Dimethicone) | 35-45 |
| Reactive silicone emulsifier (eg. Amino propyl dimethicone) | 1.0-3.0 |

C. Lotion

The following example serves to provide a general formula of representative reaction emulsion based lotion composition in accordance with the present invention. Suggested ingredient ranges are provided.

TABLE 7

Lotion Formulation

| Component | Weight Range |
|---|---|
| Oil Phase | |
| Emollients (eg. Esters and Oils) | 35-65 |
| Reactive oil emulsifier (eg. Ethylene/Maleic anhydride/propylene copolymer) | 1.0-3.0 |
| Preservative (eg. Methyl paraben) | 1.0-2.0 |
| Silicone Phase | |
| Silicone Oil (eg. Dimethicone) | 35-65 |
| Reactive silicone emulsifier (eg. Amino propyl dimethicone) | 1.0-3.0 |

All references including patent applications and publications cited herein are incorporated herein by reference in their entirety and for all purpose to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. An anhydrous emulsion composition comprising a continuous phase, a dispersed phase, and a compatibilizer present interfacially therebetween that is the reaction product of a first functional polymer dispersible in the continuous phase and a second functional polymer dispersible in the dispersed phase, the compatibilizer having at least one complementary reactive group pairing and being formed interfacially between the continuous and dispersed phases upon admixing of the continuous and dispersed phases each containing their respective first and second functional polymers dispersed therein to effect compatibilizer formation by in-situ reaction of said first and second polymers, and at least one of the continuous and dispersed phases containing a cosmetic active agent; wherein the complementary reactive group pairing is amine/cyclic anhydride.

2. The composition of claim 1, wherein the first and second functional polymers are each independently natural or synthetic polymers.

3. The composition of claim 2, wherein the natural polymers are selected from the group consisting of pullan, carrageen, glycon, cellulose, hydroxycellulose, amylose, chitosan, N,O-carboxymethylchitosan, algin and alginic acid, agar, pectin, starch, dextran, dextrin, cyclodextrin, konjac, glucomannan, chitin, pustulan, heparin, cardlan, hyaluronic acid, xantham, and combinations and derivatives thereof.

4. The composition of claim 2, wherein the synthetic polymers are selected from the group consisting of a polyolefin, a polyether, a polyester, a polysiloxane, a polyamide, a polyacrylate, a polyurethane, a polyphosphazene, a polyvinylpyrolidone, or combinations thereof.

5. The composition of claim 1, wherein the amine further includes aliphatic amines, aromatic amines, amino acids or peptides.

6. The composition of claim 5, wherein the amine is an amino acid or peptide.

7. The composition of claim 1, wherein the first functional polymer and/or the second functional polymer has two or more reactive functional groups thereon, each of the functional groups being identical in respect of each polymer.

8. The composition of claim 1, wherein one of said first and second polymers has two or more different reactive functional groups thereon, said different reactive functional groups being adapted to form two or more different complementary reactive group pairings with the complementary reactive functional group on the other of the first and second polymers.

9. The composition of claim 1, wherein both of said first and second polymers have two or more different reactive functional groups thereon, said different reactive functional groups forming two or more different complementary reactive group pairings with the respective complementary reactive functional groups on the other of the first and second polymers.

10. The composition of claim 1, wherein one or both of said first and second functional polymers have a backbone chain and at least one reactive functional group is pendant to or end-capped on the backbone chain.

11. The composition of claim 10, wherein the reactive functional group is pendant to the backbone.

12. The composition of claim 1, wherein one or both of said first and second functional polymers have a backbone chain and at least one reactive functional group is within the backbone chain.

13. The composition of claim 1, wherein the cosmetic active agent is selected from the group consisting of colorants, pigments, botanical extracts, antioxidants, emollients, humectants, moisturizers, sunscreens, keratolytics, depigmenting agents, retinoids, alpha-hydroxy acids, alpha-keto acids, lipidic compounds, anti-inflammatory agents, anti-irritants, anti-acne agents, insect repellents, skin protectants, skin penetration enhancers, exfollients, depigmenting agents, hypopigmenting agents, and compatible combinations thereof.

14. The composition of claim 13, further comprising a compatible excipient selected from the group consisting of fillers, emulsifying agents, surfactant active agents, film formers, plasticizers, solvents, chelating agents, gelling agents, thickeners, anti-foaming agents, binders, bulking agents, pH adjusters, preservatives, fragrance, stabilizers, photostabilizing agents, viscosity and/or rheology modifiers, and compatible combinations thereof.

15. The composition of claim 1, wherein the in-situ reaction does not produce a leaving group.

16. The composition of claim 1, wherein the in-situ reaction occurs at a temperature range from about 20° C. to about 120° C.

17. The composition of claim 1, wherein the in-situ reaction occurs at a pH of about 3.5 to about 9.5.

18. The composition of claim 1, wherein the in-situ reaction occurs in about one minute to about one hour after the continuous phase and the disperse phase are admixed.

19. The composition of claim 18, wherein the in-situ reaction is completed in about one minute to about ten minutes.

20. The composition of claim 1, wherein the composition is an anhydrous emulsion selected from the group consisting of oil-in-silicone, silicone-in-oil, oil-in-oil, fluoropolymer-in-oils, oil-in-fluoropolymer, fluoropolymer-in-silicone, silicone-in-fluoropolymer emulsion, and polyol-in-oil.

21. The composition of claim 20, wherein the anhydrous emulsion is further emulsified with a hydrous phase to form a double emulsion selected from the group consisting of silicone-in-oil-in-water, oil-in-silicone-in-water, fluoropolymer-in-silicone-in-water, silicone-in-fluoropolymer-in-water, fluoropolymer-in-oil-in-water, oil-in-fluoropolymer-in-water, and polyol-in-oil-in-water.

22. The composition of claim 1, wherein said first functional polymer is a polydimethylsiloxane with an amine functional group, and said second functional polymer is a polyolefin with a cyclic anhydride group.

* * * * *